United States Patent
Cho

(10) Patent No.: US 9,763,756 B2
(45) Date of Patent: Sep. 19, 2017

(54) APPARATUS AND SYSTEM FOR MAKING DENTAL IMPRESSIONS

(71) Applicant: David Cho, Citrus Heights, CA (US)

(72) Inventor: David Cho, Citrus Heights, CA (US)

( * ) Notice: Subject to any disclaimer, the term of this patent is extended or adjusted under 35 U.S.C. 154(b) by 0 days.

(21) Appl. No.: 13/804,387

(22) Filed: Mar. 14, 2013

(65) Prior Publication Data

US 2014/0272776 A1    Sep. 18, 2014

(51) Int. Cl.
*A61C 9/00*    (2006.01)

(52) U.S. Cl.
CPC .................................. *A61C 9/0006* (2013.01)

(58) Field of Classification Search
CPC ........................................ A61C 19/00–19/0093
USPC ..................... 433/34, 37, 41, 43, 44, 46, 214
See application file for complete search history.

(56) References Cited

U.S. PATENT DOCUMENTS

| | | | | |
|---|---|---|---|---|
| 1,477,098 A | * | 12/1923 | Balter ................... | A61C 9/0006 425/180 |
| 2,233,020 A | * | 2/1941 | Lubbock .............. | A61C 9/0006 433/45 |
| 2,758,374 A | * | 8/1956 | Fisher et al. ..................... | 433/37 |
| 2,860,414 A | * | 11/1958 | Brant ................... | A61C 9/0006 433/43 |
| 2,901,825 A | * | 9/1959 | Greenmun ........................ | 433/41 |
| 2,963,786 A | * | 12/1960 | Browning ........................ | 433/37 |
| 6,457,973 B1 | * | 10/2002 | Fetz ..................... | A61C 9/0006 433/37 |
| 2006/0269904 A1 | * | 11/2006 | Suchan et al. ................ | 433/213 |

* cited by examiner

*Primary Examiner* — Yogesh Patel
(74) *Attorney, Agent, or Firm* — Innovation Counsel LLP

(57) ABSTRACT

A system for making dental impressions is provided. The system includes a first dental tray and an adjustable dental tray mount for maintaining the first dental tray in a fixed position relative to an upper dental arch of a patient. The adjustable dental tray mount is capable of being mounted on the patient's head, neck or shoulders. The system further includes a flexible tooth separator with a tape-like structure and with a width equal to or greater than a distance from a tooth margin line to a gum line of a tooth of a patient. The system further includes a second dental tray, an adjustable dental tray mount for maintaining the second dental tray in a fixed position relative to a lower dental arch of a patient, and spacing structures to maintain the first dental tray and the second dental tray in position when simultaneously applied to the patient's teeth.

5 Claims, 7 Drawing Sheets

APPARATUS AND SYSTEM FOR MAKING DENTAL IMPRESSIONS

TECHNICAL FIELD

The present disclosure relates to an apparatus and system for making dental impressions.

DESCRIPTION OF THE RELATED ART

Dental practitioners are often required to make impressions of patients' teeth for various purposes, such as preparing dental prosthetics, or preparing form-fitting dental devices such as night guards, etc. The typical process of creating dental impressions involves the use of a dental tray filled with a moldable material, which is pressed against a patient's upper or lower teeth as required until the moldable material hardens and sets to create a mold or impression of the patient's teeth.

However, the devices and systems currently used to create these impressions suffer from several limitations that negatively affect the accuracy and clarity of the impressions produced. For example, dental trays usually are manually applied by the dental practitioner to the patient's teeth without any guides or other mechanical means to ensure that the patient's teeth are contacted in a consistent and stable manner. In addition, dental trays in common use typically are not adjustable in size to account for varying dental arch sizes from patient to patient, and generally require that the practitioner have multiple trays of varying sizes instead. Moreover, dental trays as currently designed do not provide for consistent contact by the moldable material with the patient's teeth, and also usually result in the excessive use of moldable material which can require additional adjustment when producing, for example, dental prosthetics. Furthermore, where an impression is required of a ground-down tooth for purposes of preparing a crown, cord-like separators typically are used to separate the tooth margin line from the gum in preparation for the impression, but these cord-like separators insufficiently separate the gum from the tooth to permit an accurate impression. And finally, where all of a patient's teeth are missing, dental trays in current use do not have means to properly position the patient's upper and lower jaws relative to each other and to the patient's temporomandibular joint (TMJ).

Accordingly, what is needed is an apparatus and system for making dental impressions that addresses these limitations.

BRIEF SUMMARY

Consistent with some embodiments, there is provided a dental tray for making dental impressions, including unperforated tray walls, a tray floor with one or more tray floor protrusions of a uniform height, and one or more inwardly-bent or curved tray wall rims.

Consistent with some embodiments, there is provided a system for making dental impressions. The system includes an upper dental tray and a lower dental tray. The upper dental tray includes an upper spacing structure with a fixed height protruding orthogonally from a plane of the upper dental tray. The lower dental tray includes a lower spacing structure with a fixed height protruding orthogonally from a plane of the lower dental tray, such that the upper spacing structure interfaces with the lower spacing structure when the upper dental tray and the lower dental tray are simultaneously applied to a patient's teeth, and the upper dental tray and the lower dental tray are fixed in position when the upper spacing structure interfaces with the lower spacing structure.

Consistent with some embodiments, there is further provided a system for making dental impressions. The system includes a first dental tray and an adjustable dental tray mount for maintaining the first dental tray in a fixed position relative to a dental arch of a patient. The adjustable dental tray mount is capable of being mounted on the patient's head, neck or shoulders. The system also includes a flexible tooth separator with a tape-like structure and with a width equal to or greater than a distance from a tooth margin line to a gum line of a tooth of a patient.

DETAILED DESCRIPTION OF THE EMBODIMENTS

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 7:
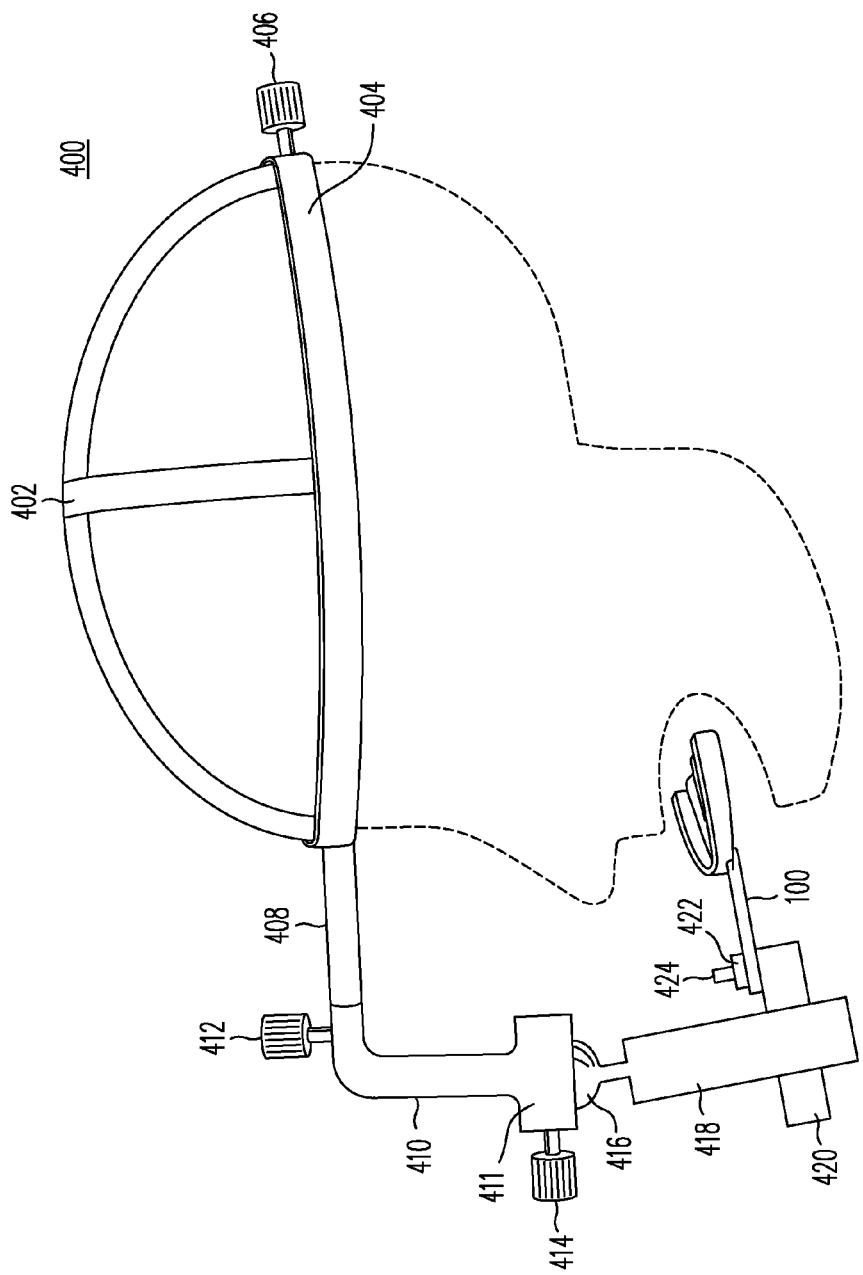
FIG. 7 is a side view of an upper dental tray holder as fitted to a patient's head.
Figure 8:
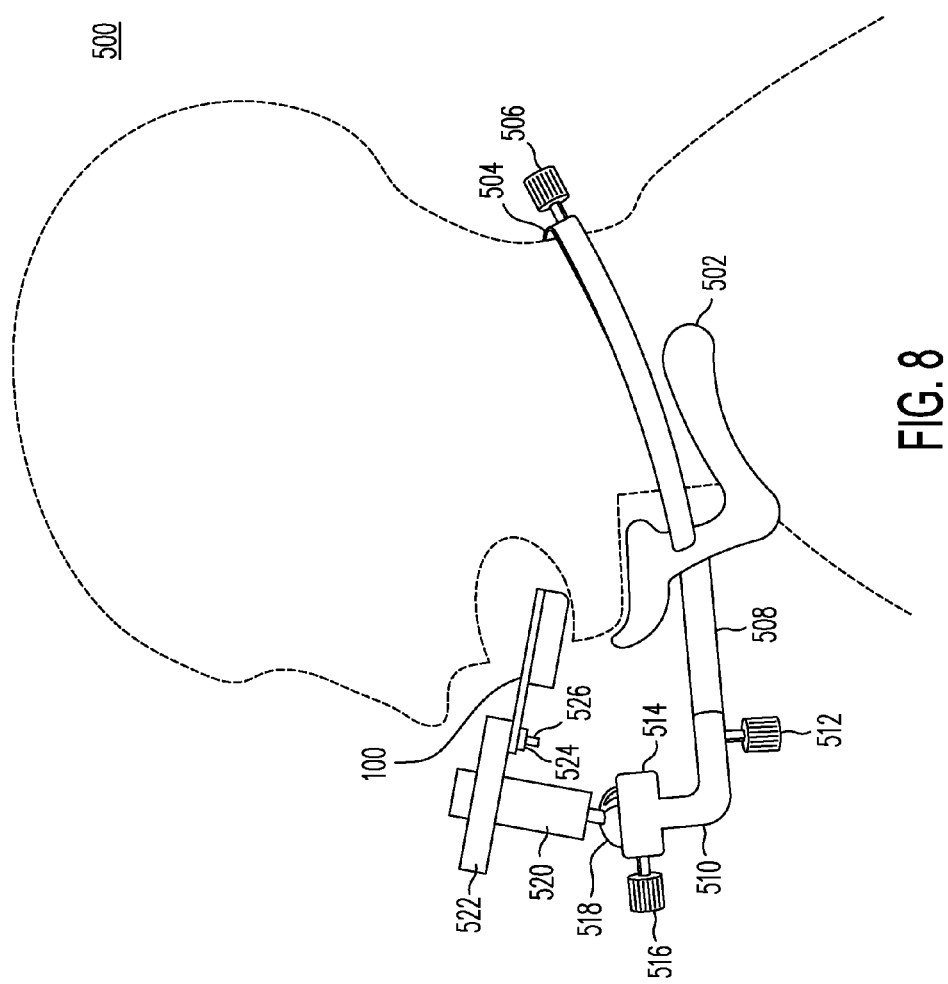
FIG. 8 is a side view of a lower dental tray holder as fitted to a patient's neck and shoulders.

FIGS. 1 through 5C illustrate a dental tray 100 according to some embodiments for creating a dental impression of a patient's teeth for use in creating dental prosthetics for the patient. FIG. 6 illustrates a separator 300 according to some embodiments for use in a system for creating a more accurate impression of a ground-down tooth for use in creating a dental prosthetic for that tooth. FIGS. 7 and 8 illustrate an upper dental tray holder 300 and a lower dental tray holder 400 according to some embodiments for use in positioning the dental tray 100 to create dental prosthetics.

With reference to FIGS. 1 through 5C, the dental tray 100 may include two dental tray mounting arms 114, each of which may include a curved portion shaped approximately to correspond to a half of a patient's dental arch, and a straight portion extending from one end of the curved portion such that each dental tray mounting arm 114 may be approximately chair-shaped. Two removable dental tray arms 102 may be removably attached to the curved portions of the dental tray mounting arms 114 by means of mounting pins 116 which hold each dental tray arm 102 in place on its corresponding dental tray mounting arm 114. Each dental tray mounting arm 114 with its dental tray arm 102 may be symmetrical about a center line (not shown) with the other dental tray mounting arm 114 with dental tray arm 102. The two dental tray mounting arms 114 may be attached to a dental tray base 110 by means of two tray arm joints 108 located approximately at the two points where the straight portions of the dental tray mounting arms 114 meet the curved portions, such that the two dental tray arms 102 form a shape approximately corresponding to a complete dental arch, and such that each dental tray mounting arm 114 rotates freely around its tray arm joint 108.

Figure 1:
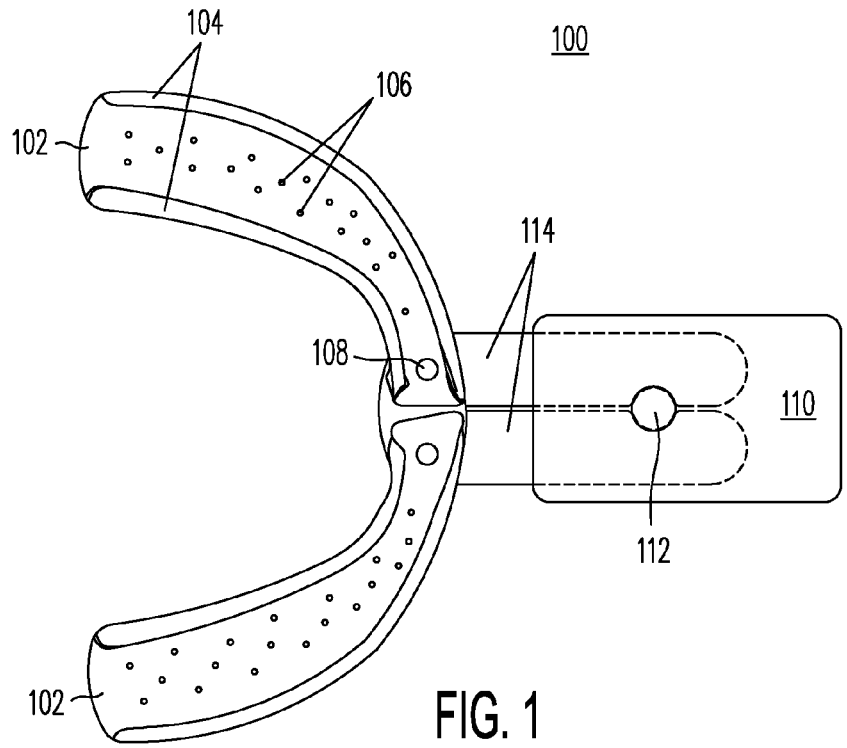
FIG. 1 is a top view of an embodiment of an adjustable dental tray for use in creating dental impressions, in a closed position.
Figure 2:
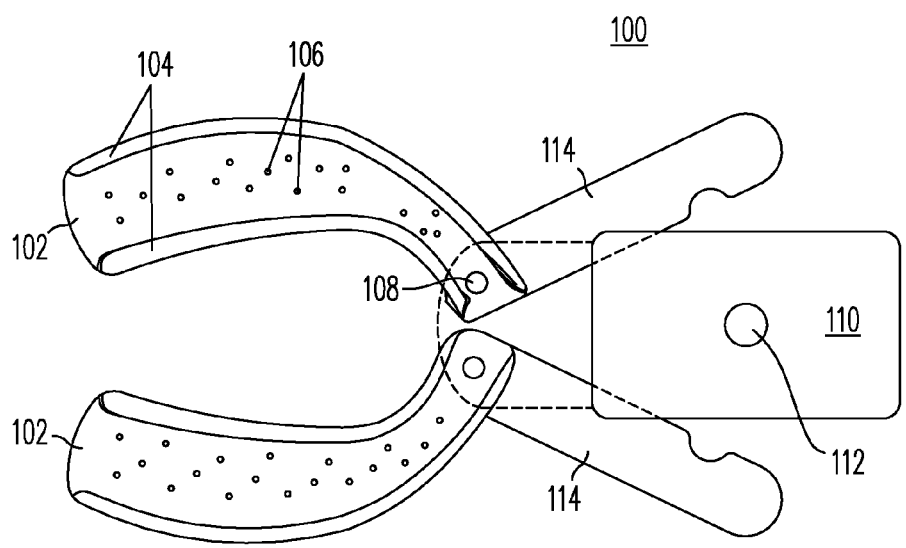
FIG. 2 is a top view of the adjustable dental tray illustrated in FIG. 1, in an open position.
Figure 3:
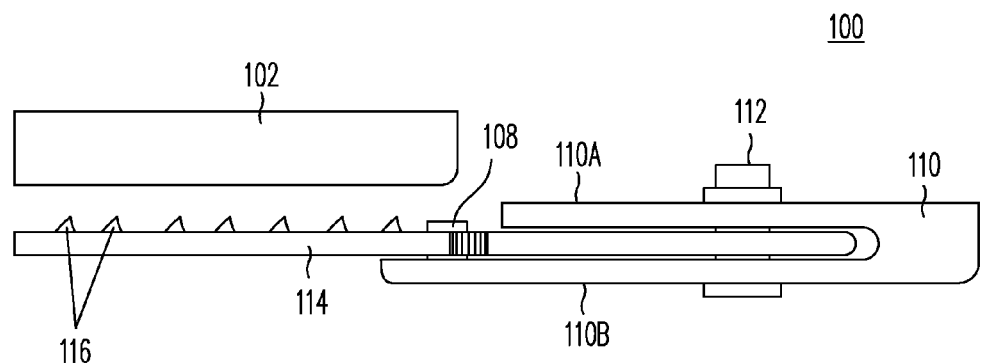
FIG. 3 is a partially-exploded side view of the adjustable dental tray illustrated in FIG. 1.
Figure 4:
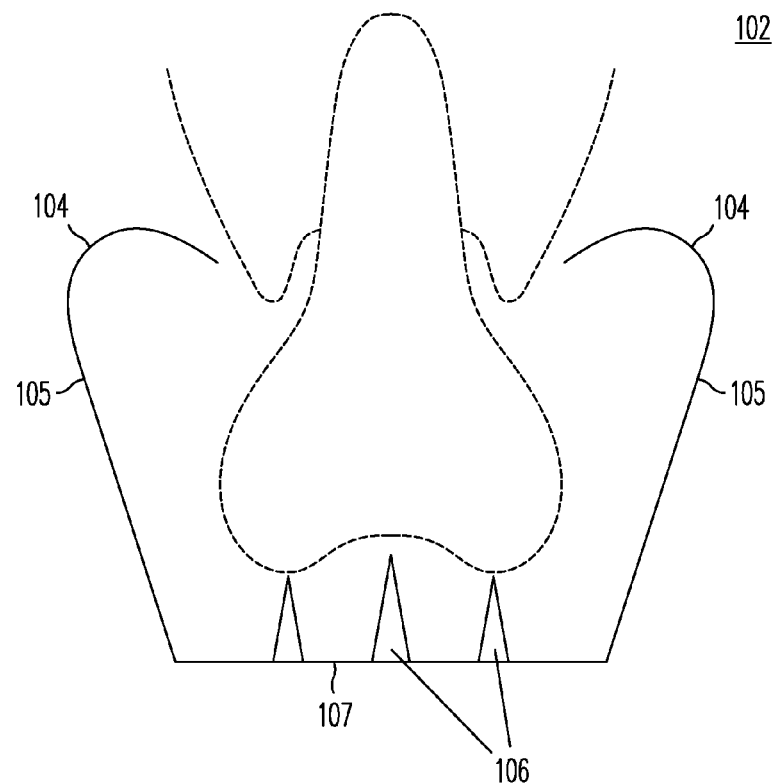
FIG. 4 is a cross-section view of one of the dental tray arms illustrated in FIGS. 1 and 2.

As shown in FIG. 3, the dental tray base 110 may include an upper tray base panel 110A and a lower tray base panel 110B, with a gap between them such that the tray arm extensions 114 may fit in the gap when rotated around the tray arm joints 108. The upper tray base panel 110A and the lower tray base panel 110B may be adjustably tightened or loosened by means of a screw 112, such that when loosened, the dental tray mounting arms 114 may freely rotate around the tray arm joints 108, and when tightened, the dental tray mounting arms 114 (and their corresponding dental tray arms 102) are thereby fixed in position. The dental tray arms 102 thus may be adjusted to more accurately conform to the shape and size of a given patient's dental arch.

Each dental tray arm 102 may include a tray floor 107 and two tray walls 105 forming a concave structure approximately fitted to a half of a patient's dental arch. According to some embodiments, the tray walls 105 may be unperforated. Mounted on the tray floor 107 is at least one tray floor protrusion 106 upon which the patient's tooth or teeth may make contact when the dental tray 100 is applied to the patient's teeth. The tray floor protrusions 106 may be pointed or otherwise shaped to minimize the size of the contact point(s) with the patient's teeth, and should be high enough to maintain a gap between the patient's teeth and the tray floor 107, but low enough such that the patient's teeth are fully encapsulated by the dental tray 100 when making a dental impression. That is, the tray floor protrusions 106 maintain the patient's teeth in a fixed position approximately centered within the concave structure formed by the tray floor 107 and the tray walls 105. At the top of each tray wall 105 is a tray wall rim 104 that may be inwardly curved or bent, further enclosing the concave structure formed by the tray floor 107 and the tray walls 105. When the dental tray 100 is filled with moldable material in preparation for taking a dental impression of a patient's teeth, the tray wall rims 104 function to hold the moldable material within the dental tray 100 after the patient's teeth have been inserted, creating tighter and more accurate contact between the moldable material and the patient's teeth. By maintaining the patient's teeth in a fixed position within the dental tray 100 by means of the tray floor protrusions 106, and by holding moldable material more tightly within the dental tray 100 by means of the unperforated tray walls 105 and the tray wall rims 104, a more accurate dental impression of the patient's teeth may be formed.

Figure 5A:
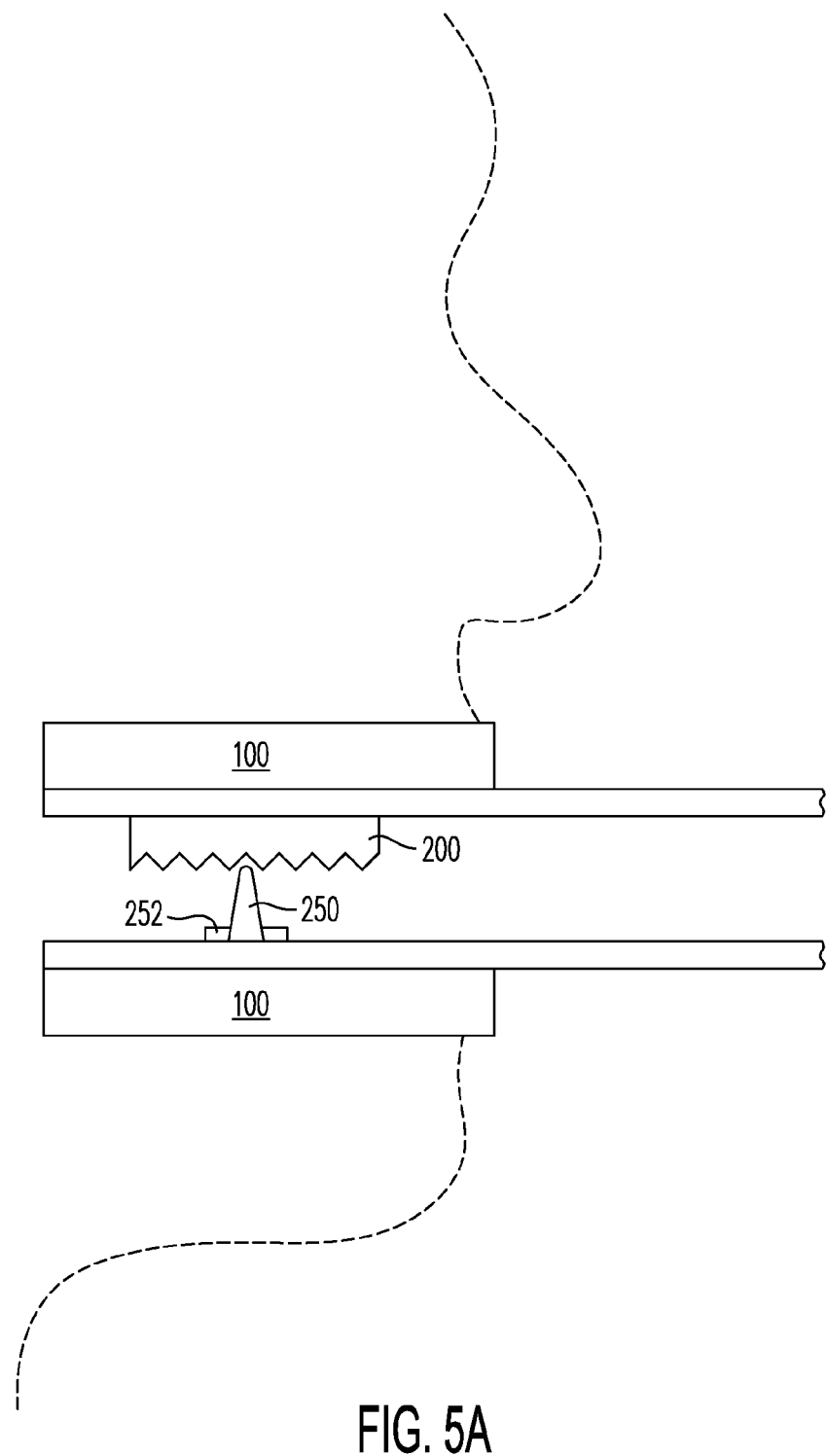
FIG. 5A is a side view of a set of dental trays with an upper spacing structure and a lower spacing structure as used with a patient's dental arches.
Figure 5B:
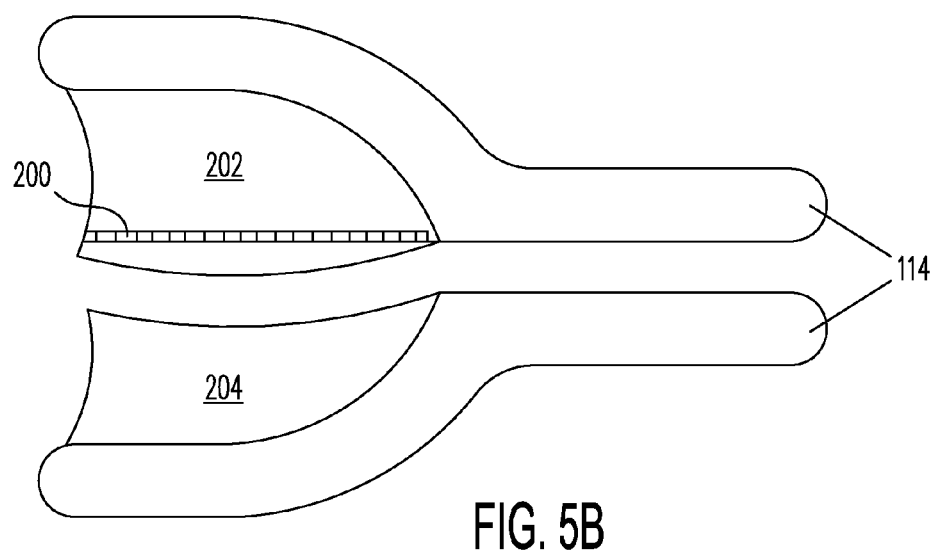
FIG. 5B is a bottom view of an upper dental tray of the set of dental trays illustrated in FIG. 5A.
Figure 5C:
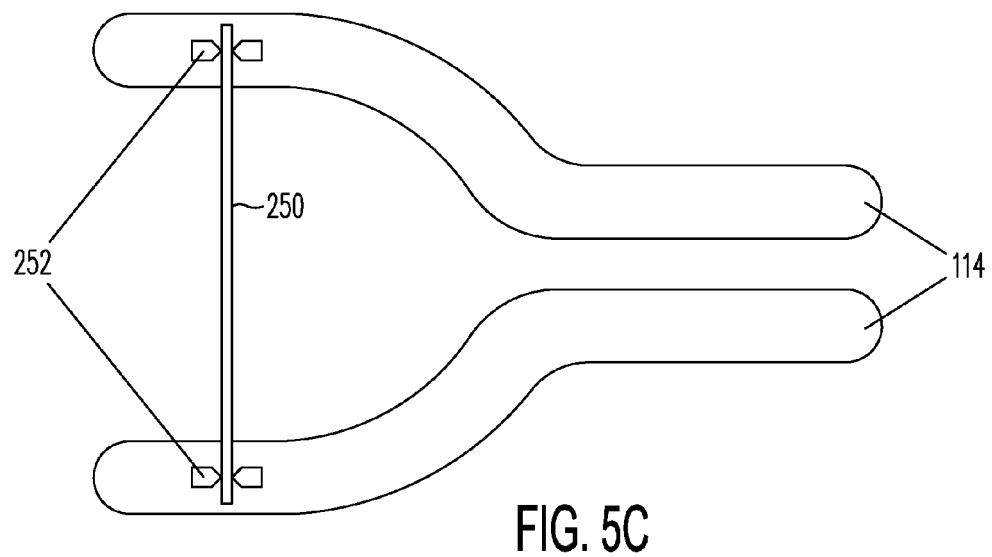
FIG. 5C is a top view of a lower dental tray of the set of dental trays illustrated in FIG. 5A.

As shown in FIGS. 5A-5C, an upper spacing structure 200 and a lower spacing structure 250 for use with a set of upper and lower dental trays 100 are illustrated. The upper spacing structure 200 may be approximately rectangular and blade-shaped and may be attached to an upper dental tray 100 such that the upper spacing structure 200 protrudes approximately orthogonally below the upper dental tray 100 and a distal edge of the upper spacing structure 200 is parallel to a plane of the upper dental tray 100. As used herein, the term "distal" refers to a direction furthest from a patient, and "proximal" refers to a direction closest to a patient. In some embodiments, the upper spacing structure 200 may be removably attached to the dental tray 100 by means of a mounting arch 202 attached to one dental tray mounting arm 114 and shaped approximately like (and slightly larger than) a half of a patient's dental arch. The spacing structure 200 may be removably attached to the mounting arch 202 so as to approximately bisect the patient's dental arch in an approximate direction that extends from a back of the patient's mouth to the front of the patient's mouth. A non-mounting arch 204 may be attached to the corresponding dental tray mounting arm 114, such that it slightly overlaps the mounting arch 202 on the surface facing the patient's dental arch. Thus, when the dental tray mounting arms 114 are adjustably widened or narrowed, the non-mounting arch 204 is able to overlap the mounting arch 202 without becoming an obstacle to the upper spacing structure 200.

Similarly, the lower spacing structure 250 may be approximately rectangular and blade-shaped, has a fixed height (e.g., 5 mm), and may be attached to a lower dental tray 100 by means of two spacing structure mounts 252 which are affixed to the curved portions of each dental tray mounting arm 114 of the lower dental tray 100. Each spacing structure mount 252 may include two mounting points which are directly opposed and which are positioned to hold an end of the lower spacing structure 250 in position such that, when both of the spacing structure mounts 252 are engaged with the lower spacing structure 250, the lower spacing structure 250 protrudes approximately orthogonally above the lower dental tray and a distal edge of the lower spacing structure 250 is parallel to a plane of the lower dental tray. The points at which the spacing structure mounts 252 contact the lower spacing structure 250 may be rounded or approximately triangular, such that the lower spacing structure 250 may be approximately maintained in position while the lower dental tray mounting arms 114 are adjustably narrowed or widened. The upper spacing structure 200 and the lower spacing structure 250 may be positioned on their respective dental trays such that when the dental trays are engaged with a patient's teeth for purposes of taking a dental impression, the distal edge of the upper spacing structure 200 and the distal edge of the lower spacing structure 250 make contact at a point with each other and are positioned approximately cross-wise relative to each other.

The distal edge of the upper spacing structure 200 may be toothed or contain regular indentations such that when contact is made with the distal edge of the lower spacing structure 250, the distal edge of the lower spacing structure 250 engages with the distal edge of the upper spacing structure 200 in a gap between two teeth or in one indentation, fixing the upper spacing structure 200 and the lower spacing structure 250 in position relative to each other at that indentation or gap. Thus, when the upper spacing structure 200 and the lower spacing structure 250 are so engaged, the dental trays are held in position such that the patient's upper and lower dental arches are at a known fixed distance from each other and are held in a set alignment relative to each other and to the patient's temporomandibular joint. Where the upper spacing structure 200 is removable, a distance between the upper and lower dental trays may be adjusted by using upper spacing structures 200 of varying heights with the lower spacing structure 250. According to some embodiments, the varying heights may include, for example, 2 cm, 2.1 cm, 2.2 cm, 2.3 cm, or 2.4 cm.

Figure 6A:
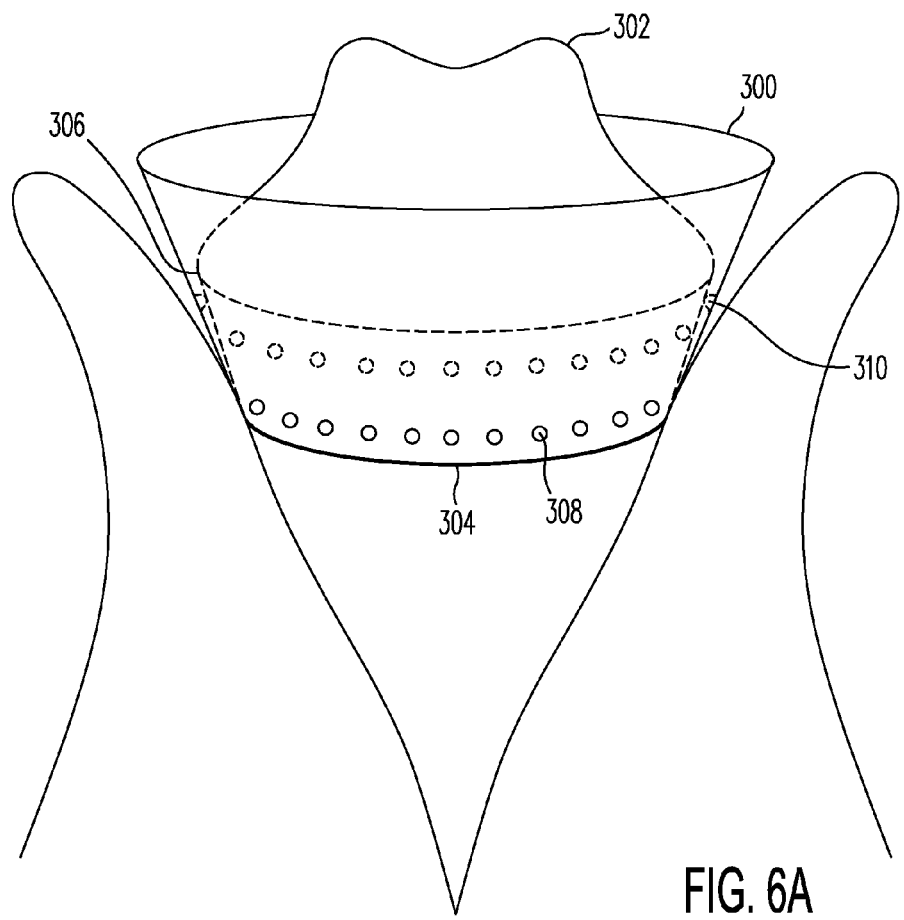
FIG. 6A is a perspective view of a separator as applied to a patient's tooth stump and gums.
Figure 6B:
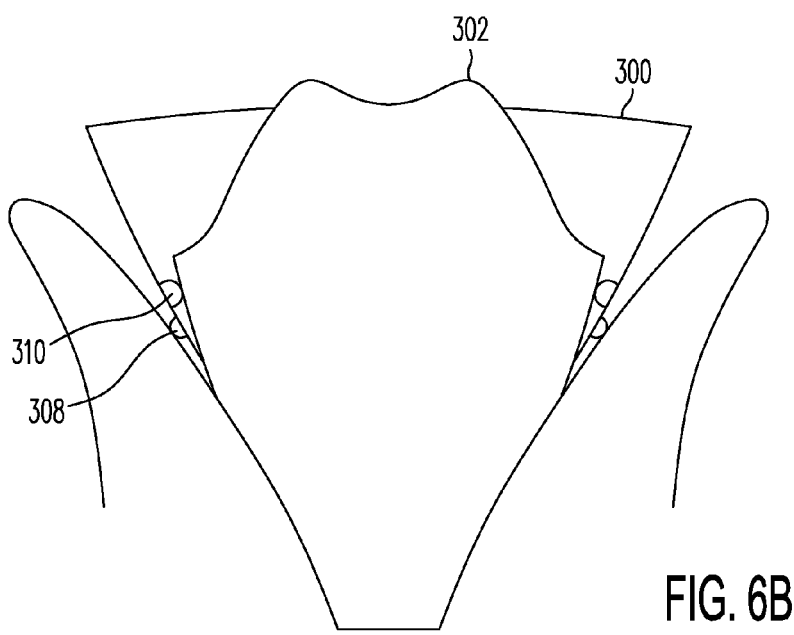
FIG. 6B is cross-section view of a separator as applied to a patient's tooth stump and gums.

FIGS. 6A and 6B illustrate a tooth separator 300 according to some embodiments for preparing a ground-down tooth to make a dental impression, and which may be used to prepare such ground-down teeth for creating a dental impression in conjunction with the dental tray described in FIGS. 1-5C. The tooth separator 300 may be flexible and tape-like in structure (i.e., a thin flat material that is longer than it is wide, such as a piece of tape or ribbon), and when used to encircle a patient's ground-down tooth 302, serves to separate a gum line 304 from a tooth margin 306 line of the patient, facilitating a more accurate dental impression. As can be seen in FIGS. 6A and 6B, the tooth separator 300 may have a width at least equal to or greater than the distance between the tooth margin line 306 and the gum line 304, preventing the gum line 304 from covering or obscuring the tooth margin line 306 when the dental impression is taken. The tooth separator 300 further may include a row of gum line protrusions 308 and a row of tooth margin protrusions 310, each in a line approximately parallel to an edge of the tooth separator 300, such that when the tooth separator 300 is used to encircle the ground-down tooth 302, the gum line protrusions 308 are aligned near the lower edge of the tooth separator 300 and extend outward toward and contact the patient's gums, while the tooth margin protrusions 310 are aligned above the gum line protrusions 308 and extend inward toward and contact the patient's tooth. The gum line protrusions 308 engage with the patient's gums and maintain the tooth separator 300 in position, while the tooth margin protrusions 310 maintain spatial separation between the ground-down tooth 302 and the tooth separator 300, facilitating a dental impression of increased accuracy.

FIG. 7 illustrates an upper dental tray holder 400 according to some embodiments for maintaining the dental tray 100 in a fixed position with respect to a patient's upper dental arch. A skullcap 402 may be shaped so as to approximately conform to a shaped of a top of the patient's head, and a head strap 404 may be adjustably loosened or tightened around a perimeter of the skullcap 402 to fix the upper dental tray holder 400 in position on top of the patient's head. A head strap tightener 406 may be tightened or loosened to fix the head strap 404 at a particular circumference. A skullcap extension 408 may protrude from the skullcap 402 approximately orthogonally and horizontally from a center of the patient's forehead, and an L-shaped positioning shaft 410 may be attached to the skullcap extension 408 such that one end of the positioning shaft 410 is coextensive with and rotates freely around an axis of the skullcap extension 408, and an other end of the positioning shaft 410 protrudes in a direction approximately perpendicular to and downwards from the skullcap extension 408. The positioning shaft 410 may be rotationally fixed in position relative to the skullcap extension 408 by loosening and tightening a positioning shaft screw 412. A distal end of the positioning shaft 410 relative to the skullcap extension 408 may include a ball joint socket 411, which may be connected to a ball joint 416 comprising one end of a dental tray shaft 418. The dental tray shaft 418 may be adjustably positioned by means of the ball joint 416, and may be fixed in position by tightening a ball joint screw 414. A tray base holder 420 may attach to the dental tray shaft 418 such that one end of the tray base holder 420 extends toward the patient's mouth, while the tray base holder 420 is fixed in place. In some embodiments, the tray base holder 420 may be attached to the dental tray shaft 418 by means of magnets. The tray base holder 420 may include a mounting bracket 422 and a bracket screw 424 at the end closest to the patient's mouth for the purpose of mounting a dental tray 100, which is inserted between the tray base holder 420 and the mounting bracket 422 and fixed in place by means of tightening the bracket screw 424. The dental tray 100 thus may be maintained in a fixed orientation relative to the patient's upper dental arch, permitting a more accurate dental impression to be taken.

FIG. 8 illustrates a lower dental tray holder 500 according to some embodiments for maintaining the dental tray 100 in a fixed position with respect to a patient's lower dental arch. A chin rest 502 may contact a patient's chin, collar, and shoulders such that the patient's chin is maintained in a fixed position. A neck strap 504 may extend from either side of the chin rest 502 and encircle the patient's neck. The neck strap 504 may be adjustably tightened or loosened so as to maintain the chin rest 502 in a fixed position relative to the patient's neck, and once adjusted, the neck strap 504 may be fixed in position by means of tightening a neck strap tightener 506. A chin rest extension 508 may extend approximately horizontally from the chin rest 502 in a forward direction relative to the patient's face, and is approximately centered beneath the patient's mouth. An L-shaped positioning shaft 510 may be attached at one end to the chin rest extension 508 so as to be coextensive with and rotate freely around the chin rest extension 508, and such that an other end of the positioning shaft 510 protrudes in a direction perpendicular to and upwards from the chin rest extension 508. The positioning shaft 510 may be rotationally fixed in position relative to the chin rest extension 508 by loosening and tightening a positioning shaft screw 512. A distal end of the positioning shaft 510 relative to the chin rest extension 508 may include a ball joint socket 514, which may be connected to a ball joint 518 comprising one end of a dental tray shaft 520. The dental tray shaft 520 may be adjustably positioned by means of the ball joint 518, and may be fixed in position by tightening a ball joint screw 516. A tray base holder 522 may attach to the dental tray shaft 520 such that one end of the tray base holder 522 extends toward the patient's mouth, and such that the tray base holder 522 is fixed in place. In some embodiments, the tray base holder 522 may be attached to the dental tray shaft 520 by means of magnets. The tray base holder 522 may include a mounting bracket 524 and a bracket screw 526 at the end closest to the patient's mouth for the purpose of mounting a dental tray 100, which may be inserted between the tray base holder 522 and the mounting bracket 524 and fixed in place by means of tightening the bracket screw 526. The dental tray 100, thus, may be maintained in a fixed orientation relative to the patient's upper dental arch, permitting a more accurate dental impression to be taken.

Although a few embodiments have been shown and described, it will be appreciated by those skilled in the art that changes may be made in these embodiments without departing from the principles and spirit of the disclosure, the scope of which is defined in the appended claims and their equivalents.

What is claimed is:
1. A system for making dental impressions, comprising:
a first dental mounting arm and a second dental mounting arm;
a first dental tray rotatably attached to the first dental mounting arm; and
a second dental tray rotatably attached to the second dental mounting arm;

a dental tray base to which the first and second dental mounting arms are attached;

wherein the first dental mounting arm and the first dental tray are coupled to the dental tray base using a common joint.

2. The system of claim 1, wherein the first dental tray comprises unperforated tray walls, one or more curved tray wall rims, and one or more tray floor protrusions of a uniform height.

3. The system of claim 1, wherein the first dental mounting arm may be adjustably rotated such that a distance to the second dental mounting arm is increased or decreased while the first dental mounting arm remains coplanar with the second dental mounting arm.

4. The system of claim 1 further comprising a flexible tooth separator that fits in the dental tray and including protrusions for maintaining spatial separation between the flexible tooth separator and the tooth.

5. The system of claim 4, wherein the flexible tooth separator further comprises protrusions for maintaining the position of the flexible tooth separator relative to a gum line of the tooth.

* * * * *